United States Patent [19]
Gerwick, III et al.

[11] Patent Number: 5,932,434
[45] Date of Patent: Aug. 3, 1999

[54] METHOD FOR IDENTIFYING WEEDS RESISTANT TO INHIBITORS OF ACETOLACTATE SYNTHASE

[75] Inventors: B. Clifford Gerwick, III, Carmel; Robert J. Eilers; Linda C. Mireles, both of Indianapolis, all of Ind.

[73] Assignee: Dow AgroSciences LLC, Indianapolis, Ind.

[21] Appl. No.: 08/037,961

[22] Filed: Mar. 26, 1993

[51] Int. Cl.[6] ............... C12Q 1/00; C12Q 1/26; C12Q 1/32; G01N 33/00
[52] U.S. Cl. ............ 435/26; 435/25; 435/4; 435/69.2; 435/189; 435/963; 436/128; 436/129; 436/130
[58] Field of Search .................. 435/26, 25, 23, 435/172.1, 172.3, 32, 817, 4, 69.2, 189, 963; 514/127; 544/321; 436/128, 129, 130

[56] References Cited

U.S. PATENT DOCUMENTS

| | | | |
|---|---|---|---|
| 4,761,373 | 8/1988 | Anderson et al. | 435/172.3 |
| 5,084,082 | 1/1992 | Sebastian | 435/172.1 |
| 5,084,086 | 1/1992 | Forney et al. | 544/321 |
| 5,102,447 | 4/1992 | Gates | 514/127 |
| 5,187,071 | 2/1993 | Fischer et al. | 435/32 |
| 5,206,135 | 4/1993 | Abell et al. | 435/4 |
| 5,231,020 | 7/1993 | Jorgensen et al. | 435/172.3 |

OTHER PUBLICATIONS

Singh et al, Analytical Biochemistry 171, 173–179 (1988).

*Primary Examiner*—Louise N. Leary
*Attorney, Agent, or Firm*—Donald R. Stuart

[57] ABSTRACT

Resistance of given plant tissue to an inhibitor of acetolactate synthase is identified by (a) combining in an aqueous medium a sample of the plant tissue, the inhibitor of acetolactate synthase, and an inhibitor of keto acid reductoisomerase;
(b) allowing time for acetolactate to accumulate;
(c) rupturing the cells;
(d) acidifying the mixture to convert any accumulated acetolactate to acetoin; and
(e) calorimetrically detecting the presence of acetoin in the mixture.

6 Claims, No Drawings

METHOD FOR IDENTIFYING WEEDS RESISTANT TO INHIBITORS OF ACETOLACTATE SYNTHASE

FIELD OF THE INVENTION

This invention provides a method for identifying weeds resistant to inhibitors of acetolactate synthase.

BACKGROUND OF THE INVENTION

Several new classes of herbicides, such as the sulfonylureas, have inhibition of acetolactate synthase as their apparent mode of action. Acetolactate synthase and acetohydroxyacid synthase are two names for the enzyme EC 4.1.3.18, which will hereinafter be referred to as ALS/AHAS. ALS/AHAS catalyzes conversion of pyruvate to acetolactate in the first step of a multistep biosynthetic pathway by which plants synthesize valine and leucine. ALS/AHAS inhibitors are of great interest as herbicides for a variety of reasons. Because vertibrates do not synthesize valine and leucine, the mode of action does not threaten vertibrates. Further, many of the newly discovered compounds are active at very low doses.

The emergence of target-site based resistance to ALS/AHAS inhibiting herbicides has, however, raised concern for the viability of this class of products. The onset of resistance has been both rapid and extensive. A total of eleven weed species resistant to ALS/AHAS inhibiting herbicides are known. These are distributed over at least four countries, eleven U.S. states, and three Canadian provinces. Well over 400 sites of Kochia resistance have been identified in North America during the past six years. Three consecutive years of sulfonylurea use in Idaho wheat prodution selected for resistance in *Lactuca serriola*. Further, resistant biotypes do not appear to suffer any significant penalty in terms of fitness. The relatively rapid emergence of resistance, coupled to high fitness of resistant biotypes, necessitates the development of resistance management strategies.

Resistance management efforts will have a significantly greater chance of succeeding if a method is available to rapidly identify resistant weeds. Ideally, a field researcher should be able to sample tissue from a putative resistant weed, test for resistance either in the field or back in the laboratory, and plan and execute an appropriate strategy all within a few hours.

SUMMARY OF THE INVENTION

Accordingly, an object of the present invention is to provide a method for quickly, easily, and reliably identifying weeds that are resistant to ALS/AHAS inhibitors.

The method can also be used to assess cross-resistance, i.e. resistance to an ALS/AHAS herbicide different from the ALS/AHAS herbicide that served as the selective agent.

The method can also be used to identify ALS/AHAS resistant crops and germplasm containing an ALS/AHAS resistant gene.

The method can also be used to screen for materials that inhibit ALS/AHAS in a selected plant specimen.

DETAILED DESCRIPTION OF THE INVENTION

More specifically, the invention provides a method for determining whether a material to be tested is capable of inhibiting acetolactate synthesis in a given sample of plant tissue which comprises the steps of:

a) combining in an aqueous medium the plant tissue sample, the material, and an inhibitor of keto acid reductoisomerase (EC 1.1.1.86, hereinafter referred to as KARI) so that acetolactate will accumulate in the mixture unless said material inhibits acetolactate synthesis;

b) allowing time for acetolactate to accumulate;

c) treating the mixture to rupture the plant cells and release the cell contents;

d) acidifying said mixture to convert any accumulated acetolactate to acetoin (3-hydroxy-2-butanone), and e) using a colorimeteric method to detect the presence of acetoin.

The basis for the method is illustrated in the following scheme, which outlines the biosynthetic route by which plants synthesize valine and leucine:

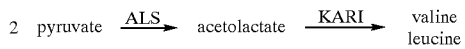

2 pyruvate $\xrightarrow{ALS}$ acetolactate $\xrightarrow{KARI}$ valine leucine

In the first step, acetolactate synthase (ALS/AHAS) catalyzes conversion of pyruvate to acetolactate. Keto acid reductoisomerase (KARI) catalyzes the following step in the sequence. The second step is blocked when an effective KARI inhibitor is present, therefore any acetolactate produced in the first step simply accumulates. But if an effective ALS/AHAS inhibitor is also present, acetolactate is not produced and none accumulates. If acetolactate accumulates in the presence of a KARI inhibitor, and a normally effective ALS/AHAS inhibitor is also present, it can be concluded that the plant is resistant to the ALS/AHAS inhibitor. In accordance with the invention, the accumulation of acetolactate is detected by converting any accumulated acetolactate to acetoin and colorimetrically detecting the presence of acetoin.

The aqueous medium used in this method preferably contains low concentrations of inorganic ions and is adjusted to a pH of about 5.5-7.5.

The plant tissue used in the method is a sample containing living cells that are normally capable of synthesizing acetolactate. The tissue sample may consist of, for example, excised whole leaves, leaf slices, or leaf disks. It is a specific advantage of the method that it does not require whole plants.

When the method is used to identify resistant weeds, the material to be tested can be any known herbicide that is known to have ALS/AHAS inhibition as its mode of action. Examples included flumetsulam, imazaquin, chlorsulfuron, metsulfuron-methyl, sulfometuron-methyl, bensulfuron-methyl, chlorimuron-ethyl, triasulfuron, thiameturon, pyrazosulfuron-ethyl, flazasulfuron, nicosulfuron, cinosulfuron, imazapyr, imazamethabenz, and imazethapyr.

The amount of ALS/AHAS inhibitor used will generally be in the range of about 0.001 to about 100 $\mu$M, depending upon the activity level of the ALS/AHAS inhibitor and the desired detection limit for resistance. ALS/AHAS inhibitors from the imidazolinone and pyrimidyl-oxy-benzoate families will likely be tested at the higher end of the range; sulfonylureas and thiazolopyrimidine sulfonanilides at the lower end.

The particular KARI inhibitor used in the method is not critical. Among the known KARI inhibitors may be mentioned 2-methylphosphinoyl-2-hydroxyacetic acid, also known as HOE 704, and N-hydroxy-N-isopropyloxamate.

Preferred KARI inhibitors are compounds of the formula

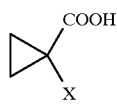

where X is COOEt, COOMe, or COOH, and salts thereof. These compounds have not previously been reported as KARI inhibitors. Although they are less active than HOE 704, and they do not have sufficient activity to be useful as herbicides, their activity is adequate for use in the method of this invention, and they are inexpensive, readily available chemicals. 1,1-Cyclopropanedicarboxylic acid (CPCA), for example, is commercially available from Aldrich Chemical Company, Inc., Milwaukee, Wis.

The amount of KARI inhibitor used will generally be in the range of about 1 nM to about 1 mM, depending upon the potency of the inhibitor. For CPCA, the prefered range is from about 50 to about 10,000 $\mu$M, and the most prefered range is 100–1000 $\mu$M.

The time allowed for acetolactate to accumulate will generally be in the range of 1–24 hours, although longer time periods still give satisfactory results. The preferred time period is 2–12 hours, depending upon the weed species and the position of the sampled leaf in the canopy. It is a specific advantage of the method that the time period required is relatively short.

After the incubation period the cells are ruptured, preferably by homogenization.

Acidification to convert the acetolactate to acetoin may suitably be carried out by bringing the plant extract to a final concentration of 0.5% $H_2SO_4$ and warming to 60° C. for 30 minutes. More generally, other acids may be used to bring about the decarboxylation. The acid will typically be present in the range of 0.1–0.5N. Time periods required, depending upon the temperature used, may range from 1–120 minutes.

Several colorimeteric methods for detetermination of acetoin are known. For example, E. Stotz and J. Raborg, J. Biol. Chem. 150:25 (1943) describe a colorimeteric procedure involving formation of a nickel salt. W. W. Westerfeld, "A Colorimetric Determination of Blood Acetoin," J. Biol. Chem. 161: 495–502 (1945) describes a method utilizing the color reaction involving reaction of acetoin with a guanidino group in the presence of base. The latter method is preferred.

More specifically, in a preferred embodiment of the invention, acetoin is calorimetrically identified by adding creatine and a basic solution of 1-naphthol to the acidified plant extract. It is preferred to successively add aqueous creatine solution followed by 1-naphthol in sodium hydroxide solution. The preferred final concentrations are 2.0 mg/mL creatine, 20 mg/mL 1-naphthol, and 0.5N NaOH. The appearance of pink color having a spectrophotometric maximum at 530 nm develops within 10–30 minutes of adding these reagents.

As reported by Westerfeld in the above identified article, other compounds containing the guanidino group can be substituted for creatine. Examples of such compounds include arginine, creatinine, guanidine carbonate, and methylguanaidine sulfate.

EXAMPLES

Seeds of velvetleaf (*Abutilon theophrasti*), redroot pigweed (*Amaranthus retroflexus*), lambsquarters (*Chenopodium album*), cocklebur (*Xanthium strumarium*) and shattercane (Sorghum bicolor) were obtained from a commercial seed supplier(Azlin Seed Co., Leland, Mass.) and SCEPTER® (a registered trademark of American Cyanamide Corporation) resistant cocklebur was a gift from Dr. William Barrentine, Delta Research and Extension Center, Stoneville, Mass.

All seeds were sown in a commercial potting mix and grown under greenhouse conditions. Plants received regular top-watering and nutrient additions. Plants were utilized in the 3–4 leaf stage for assay unless otherwise noted. In one series of experiments designed to investigate the effects of leaf position on assay, velvetleaf was grown to a height of 140 cm with 36 leaves. Differing leaves in the canopy were utilized for acetoin determination, as described below.

Leaf punches or slices (0.2–0.75 g) were incubated in 6 mL of 25% MS salt media (Gibco BRL, Gaithesrsburg, Md.) containing 500 $\mu$M CPCA and 0.025% Triton X-100 (Sigma Chemical Co., St. Louis, Mo.) at a pH of 6.8, unless otherwise indicated.

A duplicate incubation was conducted with the further addition of 10 $\mu$M flumetsulam or other ALS/AHAS inhibitor. Replication was typically 2–4 fold depending upon tissue availability. Incubation was conducted either in 10 mL plastic petri dishes or 50 mL capped plastic centrifuge tubes. As incubations in the light or dark did not significantly differ with respect to acetoin accumulation, incubations were routinely conducted in low light at 22° C. Incubation times were typically 4–12 hrs after which the tissue and media were transferred to a hand homogenizer, ground briefly, and filtered.

The levels of acetoin were determined by the above described method of Westerfeld (1945), with the following modifications. The sample was acidified by the addition of $H_2SO_4$ to a final concentration of 0.5% and warmed to 60° C. for 30 min to facilitate decarboxylation of acetolactate to acetoin. The temperature of this step is not critical and adequate decarboxylation is achieved either by using a heating block, or by simply placing the capped tube in very warm water. The desired amount of 1-naphthol was dissolved in 2.5 N NaOH and added to the sample along with creatine to a final concentration of 20 mg/mL and 2 mg/mL, respectively. Color was allowed to develop at room temperature or at 37° C. for maximum intensity. When quantification was desired, the tubes were centrifuged for 10 min at 10,000 g and the absorbance measured at 530 nm.

The effect of CPCA on acetoin accumulation in velvetleaf is reported in Table 1. In the presence of CPCA, leaf disks accumulate substantial quantities of acetoin over the concentration range of 2–100,000 $\mu$M, with a general plateau occurring above concentrations of about 100 $\mu$M (Table 1). A sharp decline at concentrations greater than 10,000 $\mu$M suggests toxicity at high concentrations by means other than KARI inhibition.

The addition of 10 $\mu$M flumetsulam with CPCA completely prevented the accumulation of acetoin (Table 1). Inhibition of ALS/AHAS by flumetsulam prevented synthesis of acetolactate, there was therefore no acetolactate available for conversion to acetoin. Although in this example the amount of acetoin was quantified for comparison, the color of the reaction tubes alone was sufficient for clearly distinguishing between the presence or absence of acetoin accumulation. Table 1 reports the results of this experiment, demonstrating the effect of differing concentrations of CPCA, accumulation in velvetleaf.

TABLE 1

| Treatment | [CPCA] ($\mu$M) | [Flumetsulam] ($\mu$M) | Reaction Color[a] | Acetoin[b] ($\mu$g/gfw/hr) |
|---|---|---|---|---|
| 1 | | | BROWN | .0 |
| 2 | 1.6 | | BROWN | .7 |
| 3 | 6.25 | | PINK | 1.0 |
| 4 | 25.0 | | PINK | 3.1 |
| 5 | 100 | | STRONG PINK | 8.5 |
| 6 | 1000 | | STRONG PINK | 10.1 |
| 7 | 10000 | | STRONG PINK | 14.3 |
| 8 | 100000 | | PINK | 4.4 |
| 9 | 100 | 10 | BROWN | 0.3 |

The ability of CPCA to induce acetoin accumulation in several weed species is shown in Table 2.

TABLE 2

| Species | [CPCA] ($\mu$M) | Reaction Color[a] | Acetoin[b] ($\mu$g/gfw/hr) | s.d.[c] |
|---|---|---|---|---|
| pigweed | 500 | pink | 3.7 | .22 |
| lambs-quarters | 500 | pink | 3.1 | .21 |
| sorghum | 500 | pink | 4.7 | .14 |
| velvetleaf | 500 | strong pink | 17.4 | 1.5 |
| cocklebur | 500 | pink | 2.6 | .30 |

[a]Color observed prior to spectrophotometric reading at 530 nm.
[b]Incubation times varied from 18 hours for cocklebur to 4 hours for velvetleaf.
[c]Standard deviation, n = 3.

These species were selected for study because of their importance in U.S. corn/soybean production and their suspected potential to develop resistance under ALS/AHAS selection pressure. In each case, a sufficient level of acetoin accumulated to enable resistance diagnosis.

A surprising finding was the speed of induced acetoin accumulation in leaf disks. The report of Schulz et. al., "The Herbicidally Active Experimental Compound HOE 704 is a Potent Inhibitor of the Enzyme Acetolactate Reductoisomerase," FEBS Lett. 238: 375–78 (1988) presented acetoin levels in intact plants and after 14 days. Sufficient amounts of acetoin accumulate in velvetleaf leaf disks for resistance diagnosis within 2 hours.

The amount of acetoin is both time and tissue level dependent. For species accumulating acetoin at slower rates such as cocklebur, the interval between tissue harvest and acetoin determination should be extended to 8–12 hours. In one series of experiments, leaf disks of velvetleaf were allowed to incubate in CPCA for 24 hours with no adverse affects on acetoin accumulation or its subsequent determination. When sampling in the field and adding leaf punches directly to CPCA media, it may be most convenient with some species to allow the samples to incubate overnight prior to resistance diagnosis.

In many cases weed escapes are likely to be quite large in size prior to being suspected as resistant biotypes. It was therefore of interest to know if mature plants and mature leaves would respond to CPCA. Velvetleaf were grown in the greenhouse to a large size and each leaf labeled according to its position in the canopy. A number of these leaves were sampled and acetoin determinations were conducted in duplicate on each leaf. The results of these determinations, demonstrating the effect of leaf position and size on CPCA induced acetoin accumulation in velvetleaf, are reported in Table 3. The data indicate that the greatest levels of acetoin in disks taken from the uppermost, youngest leaf.

TABLE 3

| Leaf Number | Leaf area class[a] | Acetoin[b] ($\mu$g/gfw/hr) |
|---|---|---|
| 1 | 1 | 31.4 |
| 2 | 2 | 21.7 |
| 3 | 2 | 18.7 |
| 7 | 3 | 13.6 |
| 10 | 1 | 18.2 |
| 13 | 1 | 15.7 |
| 14 | 3 | 10.0 |
| 16 | 2 | 18.0 |
| 17 | 3 | 14.5 |
| 19 | 1 | 12.6 |
| 20 | 3 | 15.3 |
| 21 | 2 | 12.7 |
| 24 | 3 | 12.7 |
| 26 | 1 | 19.1 |
| 29 | 3 | 15.0 |
| 31 | 1 | 18.0 |
| 33 | 3 | 14.8 |
| 34 | 3 | 15.6 |
| 35 | 3 | 20.8 |
| 36 | 3 | 18.5 |

[a]Leaf area class; 1, $\leq$40 cm$^2$; 2, 40–90 cm$^2$; 3, $\geq$90 cm$^2$.
[b]LSD (0.05) = 4.4

Interestingly, leaves of about the same size but lower in the canopy did not accumulate acetoin to the same degree. Nonetheless, these leaves, as well as older and larger leaves, all accumulated acetoin levels sufficient for resistance diagnosis. It is preferred that the youngest apical leaf be selected for resistance testing whenever possible.

The resistance diagnosis method was validated in an experiment wherein effectiveness of inazaquin at preventing CPCA induced acetoin accumulation in SCEPTER® resistant (R) and sensitive (S) cocklebur was measured. In the absence of imazaquin, leaf disks from both the R and S biotypes accumulated acetoin in the presence of CPCA. The addition of 10 or 100 $\mu$m imazaquin prevented acetoin accumulation in the S biotype, but not in the R. The visual difference in color of the reaction tubes was more than sufficient to clearly distinguish R form S. The results are reported in Table 4.

TABLE 4

| Cocklebur biotype | [CPCA] ($\mu$M) | [imazaquin] ($\mu$M) | Reaction color[a] | Acetoin[b] ($\mu$g/gfw/hr) |
|---|---|---|---|---|
| S | 500 | 0 | Pink | 2.6 |
| S | 500 | 10 | Brown | 0.7 |
| S | 500 | 100 | Brown | 0.7 |
| R | 500 | 0 | Pink | 1.6 |
| R | 500 | 10 | Pink | 1.7 |
| R | 500 | 100 | Pink | 1.3 |

[a]Color observed prior to spectrophotometric reading at 530 nm.
[b]LSD (0.05) = 0.36

As has been shown above, the invention provides a method for the rapid determination of resistance to ALS/AHAS inhibitors in field plants. The invention therefore provides an important new tool to help monitor and manage ALS/AHAS resistance. Significant advantages of the method include the short interval of time required for diagnosis, applicability to a number of important weed species in the U.S. corn/soybean rotation, low cost of reagents, and ease of use. Another significant attribute is the ready availability of a "reference control" in the diagnosis. In a preferred embodiment, leaf tissue is sampled to two containers, one containing CPCA, the other CPCA and the desired ALS/AHAS inhibitor. Both samples are worked up and compared. If acetoin is not detected in the sample incubated in the absence of the ALS/AHAS inhibitor, then clearly the diagnosis is not valid and must be repeated with greater amounts of tissue and/or a greater incubation times. The presence of this "reference control" helps to insure a valid and reliable diagnosis.

For a plant that has been shown to be resistant to one ALS/AHAS inhibitor, the method can be used to assess cross-resistance by testing additional tissue samples from the plant using different ALS/AHAS inhibitors.

The method can also be used to screen for a material that inhibits the ALS/AHAS of a preselected plant, in which case the material may or may not be a known ALS/AHAS inhibitor.

We claim:

1. A method for determining whether a material to be tested is capable of inhibiting acetolactate synthesis in a given plant tissue sample containing living cells which comprises the steps of:
   a) combining in an aqueous medium the plant tissue simple, an effective amount of the material, an effective amount of a inhibitor of keto acid reductoisomerase, wherein the keto acid reductoisomerase inhibitor is a compound of the formula

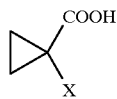

where X is COOEt, COOMe, or COOH, or a salt thereof, so that acetolactate will accumulate in the mixture unless the material inhibits acetolactate synthesis; and
   b) detecting accumulation of acetolactate.

2. The method of claim 1 wherein the ketoacid reductoisomerase inhibitor is 1,1-cyclopropanedicarboxylic acid or a salt thereof.

3. A method for determining whether a given plant is resistant to a herbicide known to have inhibition of acetolactate synthase as its mode of action, which comprises:

a) combining in an aqueous medium a fresh sample of tissue from said plant, said herbicide, and a keto acid reductoisomerase inhibitor, wherein the the ketoacid reductoisomerase inhibitor is a compound of the formula

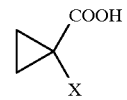

where X is COOEt, COOMe, or COOH, or a salt thereof
   b) rupturing the cells;
   c) acidifying said mixture to convert any accumulated acetolactate to acetoin, and
   d) adding a compound containing the guanidino group, 1-naphthol, and base to the mixture, so that color of the resulting mixture indicates whether acetolactate synthesis was inhibited.

4. The method of claim 3 wherein the keto acid reductoisomerase inhibitor is 1,1-cyclopropanedicarboxylic acid or a salt thereof.

5. A method for inhibiting keto acid reductoisomerase which comprises bringing it into contact with an effective amount of a compound of the formula

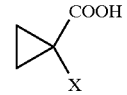

where X is COOEt, COOMe, or COOH, or a salt thereof.

6. The method of claim 5 wherein the compound is 1,1-cyclopropanedicarboxylic acid or a salt thereof.

* * * * *

UNITED STATES PATENT AND TRADEMARK OFFICE
CERTIFICATE OF CORRECTION

PATENT NO. : 5,932,434
DATED : August 3, 1999
INVENTOR(S) : B. Clifford Gerwick III, et al It is certified that error appears in the above-identified patent and that said Letters Patent is hereby corrected as shown below:

Abstract, item (e), first line, "calorimetrically" should read -- colorimetrically --.

Claim 1, line 22, "simple" should read -- sample --.

Signed and Sealed this

First Day of February, 2000

*Attest:*

*Attesting Officer*

Q. TODD DICKINSON

*Acting Commissioner of Patents and Trademarks*